(12) United States Patent  
Koch (10) Patent No.: US 10,888,412 B1  
(45) Date of Patent: Jan. 12, 2021

(54) STENT-GRAFT FOR ANASTOMOSIS

(71) Applicant: Bipore Medical Devices, Inc., Norwood, NJ (US)

(72) Inventor: Durmus Koch, Englewood, NJ (US)

(73) Assignee: Bipore Medical Devices, Inc., Norwood, NJ (US)

( * ) Notice: Subject to any disclaimer, the term of this patent is extended or adjusted under 35 U.S.C. 154(b) by 0 days.

(21) Appl. No.: 16/660,068

(22) Filed: Oct. 22, 2019

(51) Int. Cl.  
*A61F 2/06* (2013.01)  
*A61F 2/07* (2013.01)

(52) U.S. Cl.  
CPC .............. *A61F 2/064* (2013.01); *A61F 2/07* (2013.01); *A61F 2220/0033* (2013.01)

(58) Field of Classification Search  
CPC ............ A61B 17/11; A61B 2017/1135; A61B 2017/1107; A61B 2017/1139; A61B 2017/1132; A61B 2017/1103  
See application file for complete search history.

(56) References Cited

U.S. PATENT DOCUMENTS

| | | | |
|---|---|---|---|
| 3,986,828 A | 10/1976 | Hoffman, Jr. et al. | |
| 4,130,904 A | 12/1978 | Whalen | |
| 4,368,736 A | 1/1983 | Kaster | |
| 5,078,735 A | 1/1992 | Mobin-Uddin | |
| 5,104,402 A | 4/1992 | Melbin | |
| 5,123,917 A | 6/1992 | Lee | |
| 5,156,619 A | 10/1992 | Ehrenfeld | |
| 6,007,576 A | 12/1999 | McClellen | |
| 6,273,912 B1 | 8/2001 | Scholz et al. | |
| 6,743,243 B1 | 6/2004 | Roy et al. | |
| 8,343,207 B2 | 1/2013 | Rakos et al. | |
| 8,709,069 B2 | 4/2014 | Scholz et al. | |
| 2001/0037139 A1 | 11/2001 | Yencho et al. | |
| 2004/0044349 A1 | 3/2004 | Barry et al. | |
| 2005/0149166 A1* | 7/2005 | Schaeffer | A61F 2/915 623/1.13 |
| 2005/0251180 A1 | 11/2005 | Burton et al. | |
| 2008/0195125 A1 | 8/2008 | Hoffman | |
| 2009/0024208 A1 | 1/2009 | Barker | |
| 2012/0065652 A1* | 3/2012 | Cully | A61F 2/07 606/153 |
| 2013/0190787 A1* | 7/2013 | Paris | A61B 17/0643 606/153 |

* cited by examiner

*Primary Examiner* — Majid Jamialahmadi  
(74) *Attorney, Agent, or Firm* — Hoffmann & Baron, LLP (57) ABSTRACT

An anastomosis device may include an anchor including a base with an opening and a riser portion securably associated with the base. The base is configured to be disposed within a body lumen. The riser portion includes at least one attachment point with a tubular and hollow graft secured directly to the at least one of attachment point of the riser portion. The at least one attachment point of the riser portion is free of sutures or pins traversing portions of the graft proximal the riser portion. The at least one of attachment point of the riser portion may be in the form a tip of a hook. The anastomosis device may further include at least two additional attachment points for securing the graft to the riser portion.

18 Claims, 5 Drawing Sheets

STENT-GRAFT FOR ANASTOMOSIS

FIELD OF THE INVENTION

The present invention is related to a stent-graft assembly for anastomosis. More particularly, the present invention is related to a stent-graft assembly for end-to-side, sutureless anastomosis.

BACKGROUND OF THE INVENTION

An anastomosis is typically a surgical connection between two tubular vessels, such as blood vessels. For example, when part a blood vessel is surgically removed, the two remaining ends may be sewn or stapled together, i.e., an end-to-end anastomosis. A side-to-side anastomosis involves a connection between two vessels lying or positioned beside each other. An end-to-side anastomosis involves a connection of the end of one vessel to a side of another vessel. When the vessels are all bodily lumens, any anastomosis typically involves sewing, suturing, or stapling of the vessels.

In the case where one of the vessels is an artificial or synthetic graft, an anastomosis with a native vessel is often accomplished through the use of sutures. For example, U.S. Pat. No. 5,156,619 to Ehrenfeld describes a woven or knitted graft having a flanged portion for suturing the graft to a native vessel for an end-to-side anastomosis. End-to-side anastomoses have also been proposed with stent-type devices. These devices are described are requiring sutures, adhesives, staples or other complicated mechanical components for achieving end-to-sides anastomoses. See, for example, U.S. Pat. No. 6,007,576 to McClellan (requiring complicated, slidingly engagable and interlocking tubular elements); U.S. Patent Application Publication No. 2001/0037139 to Yencho et al. (requiring prongs and inter-engaging deformable elements); U.S. Patent Application Publication No. 2005/0251180 to Burton et al. (requiring, for example sutures and/or glue); and U.S. Patent Application Publication No. 2008/0195125 to Hoffman (requiring complicated stent structures and suturing of the stent structures to graft tubes).

As such, there is a need in the art for a simple, but effective, stent-graft assembly for end-to-side anastomosis which does not require the use of sutures, staples, adhesives or other complicated connection means common in the prior art to secure to the stent-graft assembly to a bodily lumen. Moreover, there is a need in the art for a stent-graft assembly for end-to-side anastomosis having simple, but effective, securement of the components forming the assembly without the use of use of sutures, staples, adhesives, or other extraneous connection means common in the prior art.

SUMMARY OF THE INVENTION

In one aspect of the present invention, an anastomosis device may include an anchor having a base with an opening and a riser portion securably associated with the base, the base being configured to be disposed within a body lumen, the riser portion having at least one attachment point; and a tubular and hollow graft secured directly to the at least one of attachment point of the riser portion, the at least one attachment point of the riser portion being free of sutures, adhesives, staples, or pins traversing portions of the graft proximal the riser portion and thus not relying on traditional or prior art connection devices.

The anastomosis device may further include a tubular stent disposed within at least a portion of the graft to provide a stent-graft. The tubular stent may be a coil stent or other stent structures, such as but not limited to a braided stent, a woven stent, a knitted stent, a mesh stent, a slotted stent, a zigzag stent, and the like.

The graft may have a textile construction of knitted or woven yarns. The graft may be securably disposed over the stent. The graft may be free of sutures, staples, adhesives, or other connection elements between the graft and the stent, and the stent may be free of barbs or other connection elements for engaging the graft.

The at least one attachment point may be a detent having a tip directed towards the base. The tip may be a vertex, such as an apex of a truncated triangle, or a cusp, such as an end of intersecting curves. The tip may be pointed, elongated, and/or curved. The tip is configured to engage an inner portion of the graft. Desirably, the tip engages the inner portion of the graft without puncturing through the wall of the graft. The anastomosis device may further include at least two additional attachment points, each of the at least two additional attachment points being a detent having a cusp or edge, defined or configured by, for example, intersections of linear lines, curves, and a combination of a linear line and a curve, disposed in a direction towards the base and configured to engage an inner portion of the graft. The at least two additional attachment points may be disposed on opposing sides of the riser portion.

The anastomosis device may further include an elongate hook member having opposed first and second ends. The first opposed end may include a hook base secured to the base of the anchor. The second opposed end may have a tip, cusp, or edge disposed in a direction towards the base. The tip, cusp or edge of the hook member may be the at least one attachment point described above.

The anastomosis device may yet further include an arm having one end secured to a portion of the outer surface of the riser and a second end not secured to the outer surface of the rise and disposed above or way from the outer surface of the riser. The second end of the arm may serve as another attachment point for the graft.

In another aspect of the present invention, an anastomosis device may include (a) an anchor comprising: (i) an elongate and curved base comprising: first and second opposed ends defining a longitudinal axis therein between and curved sides disposed downwardly from the longitudinal axis of the base; an opening disposed between the first and second opposed ends, the opening being defined by an orifice wall boundary, the orifice wall boundary having first and second generally opposed or displaced orifice wall portions; (ii) a hook member securably disposed to the curved base proximal to the first opposed orifice wall portion; (iii) an elongate curved riser comprising: first and second opposed ends defining a longitudinal axis therein between, the first opposed end of the riser being disposed to the base proximal to the second opposed orifice wall portions; and first and second opposed curved sides disposed downwardly from the longitudinal axis of the riser, the first and second opposed sides each having a terminal anchoring point; and (b) a tubular and hollow graft secured to the anchor at the hook member and secured to the anchor at the terminal anchoring points of the riser. The graft may be free of sutures, pins, staples, or other conventional attachment devices at graft portions proximal to the anchor.

The opening in the curved base of the anchor may be a circular, including a substantially circular, opening defined by a radius. The curved sides of the riser proximal to the base may have a radius of curvature equal, including substantially equal, to the radius of the opening. The radius of curvature of the curved sides of the riser along its longitudinal extent may be constant or may vary.

The hook member may include a base portion secured to the curved base of the anchor and an opposed tip portion with the graft being securably disposed thereat. The opposed tip portion may be disposed in a direction towards the base of the anchor.

The anastomosis device may further include an arm having one end secured to a portion of the outer surface of the riser and a second end not secured to the outer surface of the rise and disposed above or way from the outer surface of the riser. The second end of the arm may serve as another attachment point for the graft.

The curved base, the riser, and the hook member may be formed from or include a biocompatible metallic material. The metallic material may include a nickel-titanium alloy, such as NITINOL. The present invention, however, is not limited to the use of NITINOL to form the anchor, and other biocompatible materials may suitably be used. Useful biocompatible materials include biocompatible metals and biocompatible alloys. Desirably, biocompatible metals or alloys include NITINOL, stainless steel, cobalt-based alloy such as ELGILOY, platinum, gold, titanium, tantalum, niobium, and combinations thereof. The riser and the hook member may be welded to the curved base. Alternatively, the curved base, the riser, and the hook member may be a one-piece, monolithic structure.

The anastomosis device may further include a tubular stent disposed within the graft or within portions of the graft. The tubular stent may be a coil stent or other stent structure, such as but not limited to a braided stent, a woven stent, a knitted stent, a mesh stent, a slotted stent, a zigzag stent, and the like. The graft may have a textile construction of knitted or woven yarns. The graft may be securably disposed over the stent and be free of sutures, staples, pins, adhesives, or other conventional attachment devices between the graft and the stent.

In another aspect of the present invention, an anastomosis device may include (a) an anchor comprising: (i) an elongate and curved base comprising: first and second opposed ends defining a longitudinal axis therein between and curved sides disposed downwardly from the longitudinal axis of the base; an opening disposed between the first and second opposed ends, the opening being defined by an orifice wall boundary, the orifice wall boundary having first and second generally opposed or displaced orifice wall portions; (ii) a hook member securably disposed to the curved base proximal to the first opposed orifice wall portion; (iii) an elongate curved riser comprising: first and second opposed ends defining a longitudinal axis therein between, the first opposed end of the riser being disposed to the base proximal to the second opposed orifice wall portions; and first and second opposed curved sides disposed downwardly from the longitudinal axis of the riser, the first and second opposed sides each having a terminal anchoring point; (iv) an arm having a first end secured to a portion of an outer surface of the riser and a second end disposed away from the outer surface of the riser; and (b) a tubular and hollow graft secured to the anchor at the hook member, at the terminal anchoring points of the riser, and at the second end of the arm.

These and other features and advantages of the present invention will become apparent from the following detailed description of illustrative embodiments thereof, which is to be read in connection with the accompanying drawings.

Corresponding reference element numbers or characters indicate corresponding parts throughout the several views of the drawings.

DETAILED DESCRIPTION OF THE INVENTION

Figure 1:
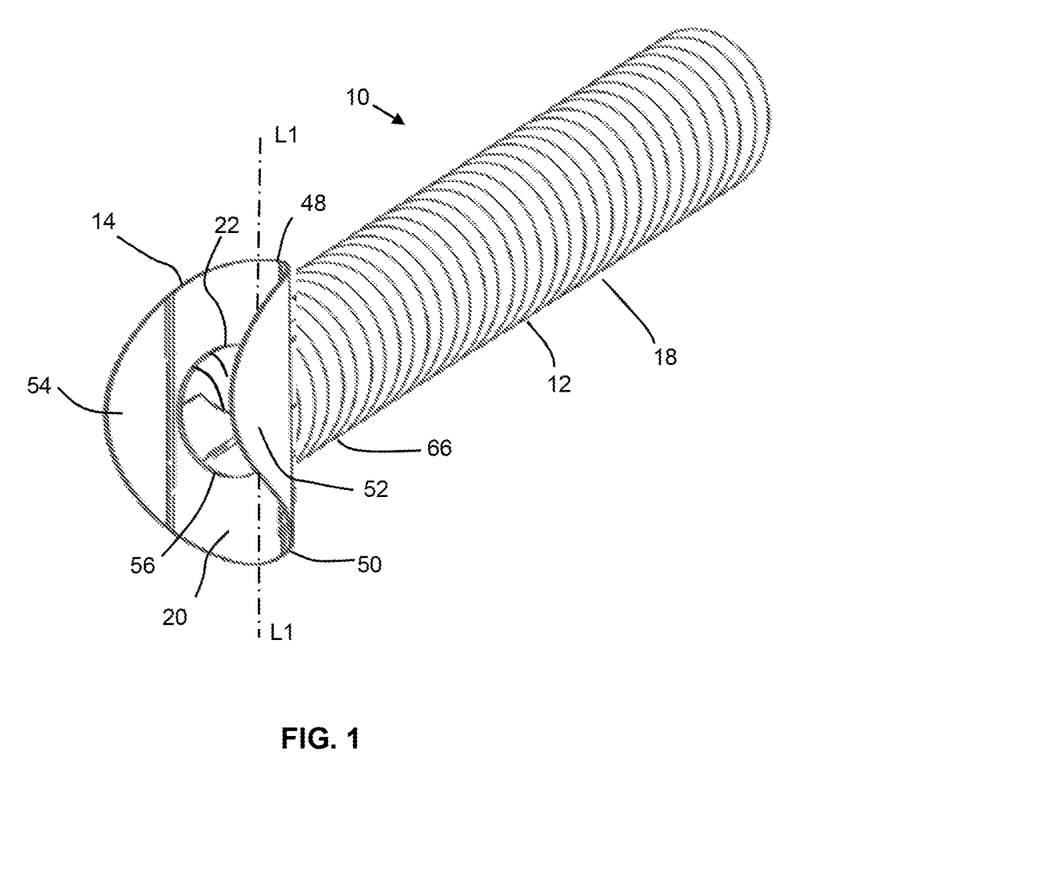
FIG. 1 is a perspective view of an anastomosis device of the present invention having a graft securably disposed to an anchor.

FIG. 1 is a perspective view of the anastomosis device 10 of the present invention. The anastomosis device includes a graft 12 and an anchor 14. The graft 12 may further include a stent 16, thereby providing a stent-graft 18. The graft 12 or stent-graft 18 is securably disposed to the anchor 14. The securement of the graft 12 or the stent-graft 18 to the anchor 14 is described below. Nevertheless, the securement of the graft 12 or the stent-graft 18 to the anchor 14 is desirably accomplished without the use of sutures, pins, staples, ties, adhesives, or the like.

Figure 2:
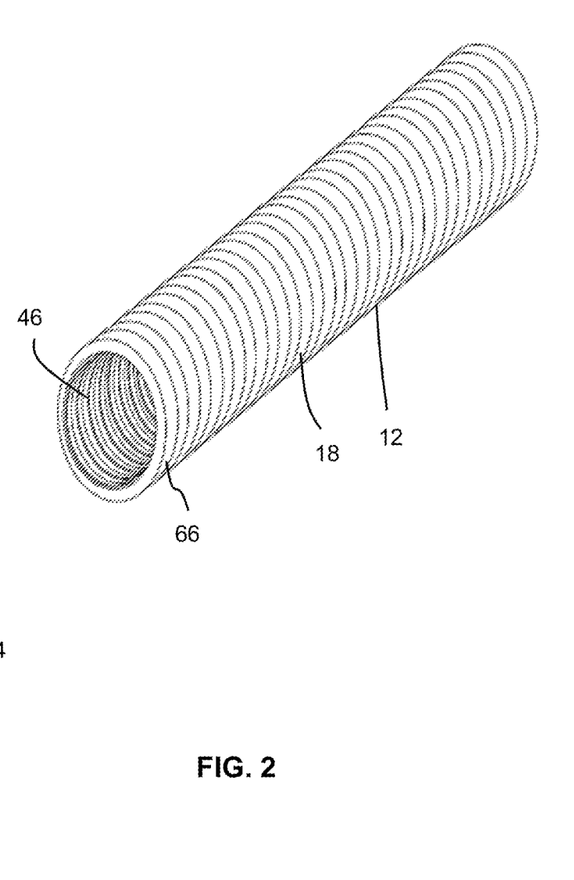
FIG. 2 is a perspective view of the anastomosis device of FIG. 1 showing the graft and the anchor prior to securement of the graft to the anchor.

FIG. 2 depicts the graft 12 or the stent-graft 18 prior to being securably disposed to the anchor 14. The graft 12 or stent-graft 18 may simply be slid over the anchor 14 to securably dispose the graft 12 or stent-graft 18 thereat. In brief, the anchor 14 includes a base 20 having an opening or orifice 22 there through. A riser or riser portion 24 of the anchor 14 is configured to be disposed proximal and/or inserted into the open lumen 46 of the graft 12 or the stent-graft 18. Desirably, graft portions 66 that are proximal to the anchor 14 are free of sutures, staples, pins, ties, adhesives, and the like. Further details of the anchor 14 is described below in conjunction with FIGS. 3 to 6.

Select graft-attaching or prosthesis-attaching portions of the anchor 14, such as the below described tip portion 44 of the hook member 36 and/or the below described terminal anchor points 26, 28 of the riser 24, engage an interior graft wall portion of the graft 12 or stent-graft 18 to secure or affix the graft 12 or stent-graft 18 thereat. The nominal or quiescent diameter or radius of the riser 24 and/or the nominal radial distance of the graft-attaching or prosthesis-attaching portions of the anchor 14 from the longitudinal axis of the riser 24, is larger than the nominal or quiescent radius or diameter of the graft 12 or stent-graft 18 such that the graft-attaching or prosthesis-attaching portions of the anchor 14 frictionally and non-piercingly engage the interior wall portion of the graft 12 or stent-graft 18. In other words, the graft 12 or stent-graft 18 engages or clasps the graft-attaching or prosthesis-attaching portions of the anchor 14 for securement thereat. The anchor 14 and/or the graft 12 or stent-graft 18 have sufficient resiliency to allow such inter-engaging after the graft 12 or stent-graft 18 is slid over the riser 24. The riser 24 may be radially compressed from its quiescent state to facilitate placement of the graft 12 or stent-graft 18 over the riser 24. In addition, the graft wall of the graft 12 may be a crimped graft wall. Such crimping also provides interior graft surfaces for enhanced inter-engaging of the graft 12 or stent-graft 18 and the graft-attaching or prosthesis-attaching portions of the anchor 14. The nominal or quiescent inner diameter of graft 12 may be from about 20 percent to about 50 percent larger in diameter than the outer diameter of the riser 24, desirably from about 30 percent to about 40 percent. These relative dimensions are non-limiting, and other dimensions may suitably be used.

The anchor includes an elongate base 20. The base 20 includes first and second opposed ends 48, 50 defining a longitudinal axis L1 therein between and curved sides 52, 54 disposed downwardly, e.g., in a direction away from the riser 24, from the longitudinal axis L1 of the base 20. The curved sides 52, 54 of the base 20 provide for a curved base 20 in the general shape of a saddle. The base 20 includes first and second opposed ends 48, 50, defining a longitudinal axis L1 therein between. The ends 48, 50 and the sides 52, 54 are free of sharp points or sharp edges to provide an atraumatic base 20, i.e., a base 20 that will not harm or cause undue trauma to a body vessel.

The atraumatic base 20 is made from a thin flexible, metallic material. One useful metallic material is nickel-titanium alloy (NiTi), such as NITINOL. Other materials such as, but not limited to, stainless steel, cobalt-based alloy such as ELGILOY, titanium, tantalum, niobium and combinations thereof. Desirably, the thickness of the base 20 is from about 0.001 inches (or about 0.025 mm) to about 0.003 inches (or about 0.076 mm), more desirable from about 0.002 inches (or about 0.51 mm) to about 0.0025 inches (or about 0.064 mm). The different components of the base 20 may be made from the same material or may be made from different materials. Desirably, the different components of the base 20 are made from the same material. The base 20 may be deployed through surgical techniques or percutaneous endovascular techniques.

The materials, dimensions and geometry, i.e., atraumatic, curved and saddle-shaped base, thin base 20 of the present invention permit effective end-to-side, sutureless anastomosis. The two sides 52, 54 of the base 20 may be moved towards one and the other, such as squeezing the sides 52, 54 towards each other. The base 20 may then be inserted through a slit or cut (not shown) in a body lumen, such as a blood vessel. After the sides 52, 54 return to their quiescent shape, such as the shape depicted in FIGS. 3 and 4, the base 20 is securable disposed or delivered within the body lumen.

The base 20 of the anchor 14 includes an opening 22 disposed between the first and second opposed ends 48, 50 of the base 20. The opening 22 is defined by an orifice wall boundary 56. The orifice wall boundary 56 includes first and second opposed orifice wall portions 58, 60 having additional anchor members or additional anchor components disposed thereat. The opening 22 is depicted as being circular, including substantially circular or even approximately circular, such as oval (not shown).

A hook member 36 may be securably disposed to the curved base 20 proximal to the first opposed orifice wall portion 58. The hook member 36 includes a base portion 42 secured to the curved base 20 of the anchor 14 and an opposed tip portion 44. The opposed tip portion 44 may be disposed in a direction towards the base 20 of the anchor 14. The graft 12, after being disposed over the anchor 14 may be being secured to the tip portion 44 of the hook member 36.

Figure 3:
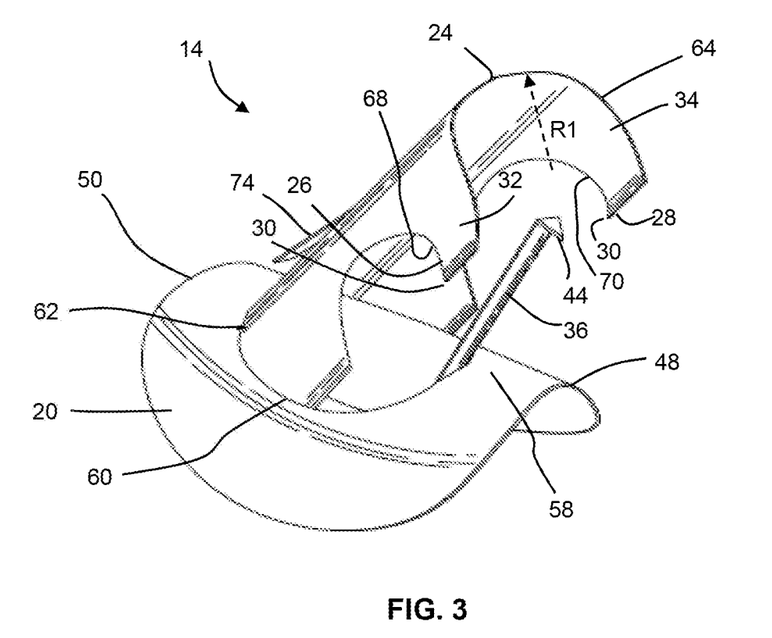
FIG. 3 is a front perspective view of the anchor of the anastomosis device of FIG. 1.
Figure 4:
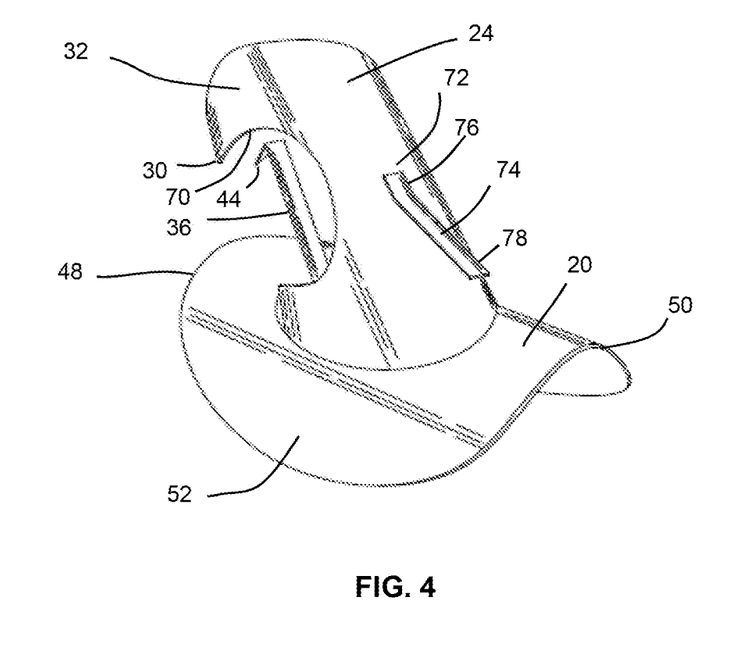
FIG. 4 is a rear perspective view of the anchor of the anastomosis device of FIG. 1.

Moreover, as depicted in FIGS. 3-6, an arm 74 may be secured to or integral with the anchor 14. More particularly, the arm 74 may be secured to or integral with the riser 24 of the anchor 14. The arm 74 is an elongate member having a first end 76 and an opposed second end 78. The first end 76 of the arm 74 is secured to or integral the riser 24 proximal to or at a riser portion 72. The riser 24 has an inner surface or inside wall 80 opposed from an outer surface or outside wall 82. The riser portion 72 is on the outer surface or the outside wall 82 of the riser 24. The second end 78 of the arm 74 is not secured to the riser 24, but rather is disposed above the outer surface 82 of the riser 24. In addition the second end 78 of the arm 74 is disposed in a direction towards the base 20. The second end 78 of the arm 74 is configured to securably engage the graft 12 after the graft 12 is disposed over the anchor 14. As best observed in FIG. 6, the arm 74 is disposed at an acute angle of about 20 degrees from the outer wall 82 of the riser 24. Such an angle is non-limiting and other angles may be used. For example, angles from about 10 degrees to about 30 degrees may be used. Further, while the arm 74 is depicted as being a generally straight, elongate member in FIG. 6, the present invention is not so limited. For example, as depicted in FIG. 4, the first end 76 of the arm 74 may have a base portion substantially parallel to the outside wall 82 of the riser. Moreover, if desired, the arm 74 itself may be curved, either convexly or concavely (not shown). Furthermore, if desired, the second end 78 of the arm 74 may have a pointed tip (not shown).

The second end 78 of the arm 74 is configured to engage an inner portion of the graft 12 opposite from an inner portion of the graft 12 engaged by the tip 44 of the elongate hook member 36. As illustrated in FIGS. 3-6, the second end 78 of the arm 74 is configured to engage an inner portion of the graft 12 which is about 180 degrees away from the inner portion of graft 12 engageable with the tip 44 of the elongate hook member 36. Such a degree of separation is non-limiting, and other degrees of separation such as from about 160 degrees to about 200 degrees may suitably be used.

The anchor 14 further includes an elongate curved riser 24 disposed about the opening 22 or a portion of the opening 22 of the base 20. The riser 24 then extends upwardly or away from the base 20. As depicted in, for example FIG. 2, the riser 24 may be disposed an angle of about 45 degrees, which is the approximate acute angle between the longitudinal axis L1 of the base 20 and the longitudinal axis L2 of the riser 24. The present invention is not limited to an orientation of 45 degrees between the base 20 and the riser 24, and other suitable angles may be used, including acute angles, obtuse angles and perpendicular angles. Desirably, the angle between the base 20 and the riser 24 may be from about 20 degrees to about 90 degrees, including from about 30 degrees to about 60 degrees. An appropriate angle may be chosen to accommodate various anatomical features of the body.

The riser 24 or riser portion 24 further includes first and second opposed ends 62, 64 defining a longitudinal axis L2 therein between. The first opposed end 62 of the riser 24 may be disposed to the base 20 proximal to the second opposed orifice wall portion 60. The first and second opposed curved sides 32, 34 are desirably disposed downwardly from the longitudinal axis L2 of the riser 24. The first and second opposed sides 32, 34 may each have a terminal anchoring point 26, 28. The terminal anchoring points 26, 28 are desirably an integral feature of the riser 24. Alternatively, the terminal anchoring points 26, 28 may be separate components, such as barbs that are secured to the riser through, for example welding. The terminal anchoring points 26, 28 may be formed from cut-outs 68, 70 of the riser sides 30, 32, respectively. The anchor 14 may be formed by various other techniques including stamping, laser cutting, three-dimensional (3D) or additive printing, and the like. While the cut-outs 67, 70 are depicted as being semi-circles in FIGS. 3, 4, and 6, other cut-out shapes may suitably be used. The terminal anchor points 26, 28 may be configured to be intersections between a line and a curve or circle, as depicted in, for example, FIG. 3. The present invention is, however, not so limited. The terminal anchor points 26, 28 may be configured to be intersections between lines (not shown) or between curves (not shown). Further, the terminal anchor points 26, 28 may be pointed, elongated, curved, and/or rounded.

The tubular and hollow graft 12 and/or stent-graft 18 may be secured to the anchor 14 via the tip portion 44 of the hook member 36, the second end 78 of the arm 74, and/or the terminal anchoring points 26, 28 at the cutouts 68, 70 of the riser 24. As such the graft 12 or stent-graft 18 is frictionally engaged to the attachment points 44, 26, 28, 78 of the riser 24. No additional sutures, staples, pins, adhesives, or the like are necessary for securing the graft 12 or stent-graft 18 to the anchor 14. The resilient, outwardly bias property of the anchor 14, for example the bias to return to a quiescent or substantially quiescent configuration after a compressive force at the curved sides 32, 34 of the riser 24 is removed, serves to maintain the inter-engagingly affixation between the anchor 14 and the graft 12 or stent-graft 18.

The present invention, however, does not require (i) the tip portion 44 of the hook member 36, (ii) the second end 78 of the arm 74, and (iii) the two terminal anchoring points 26, 28 at the cutouts 68, 70 of the riser 24 to adequately secure the graft 12 to the anchor 14. Any two or even one of the items (i) through (iii) may be used to adequately secure the graft 12 to the anchor 14. Thus, the anastomosis device 10 of the present invention may use all or any of (i) the tip portion 44 of the hook member 36, (ii) the second end 78 of the arm 74, and (iii) the two terminal anchoring points 26, 28 at the cutouts 68, 70 of the riser 24 to adequately secure the graft 12 to the anchor 14. Desirably, the anastomosis device 10 of the present invention may use (i) the tip portion 44 of the hook member 36, (ii) the second end 78 of the arm 74, and (iii) the two terminal anchoring points 26, 28 at the cutouts 68, 70 of the riser 24 to adequately secure the graft 12 to the anchor 14.

Graft 12 or portions of the graft 12 of the present invention may include wall portions made from any biocompatible, durable material, including, for example polyethylene; polypropylene; polyvinyl chloride; polytetrafluoroethylene (PTFE); fluorinated ethylene propylene; fluorinated ethylene propylene; polyvinyl acetate; polystyrene; poly(ethylene terephthalate); naphthalene dicarboxylate derivatives, such as polyethylene naphthalate, polybutylene naphthalate, polytrimethylene naphthalate and trimethylenediol naphthalate; polyurethane, polyurea; silicone rubbers; polyamides; polyimides; polycarbonates; polyaldehydes; polyether ether ketone; natural rubbers; polyester copolymers; silicone; styrene-butadiene copolymers; polyethers; such as fully or partially halogenated polyethers; and copolymers and combinations thereof. As used herein, textile materials are filaments or yarns that are woven, braided, knitted, filament-spun, and the like to form textile graft material. Desirably, the graft 12 of the present invention is a woven poly(ethylene terephthalate) or woven PET textile graft.

Figure 5:
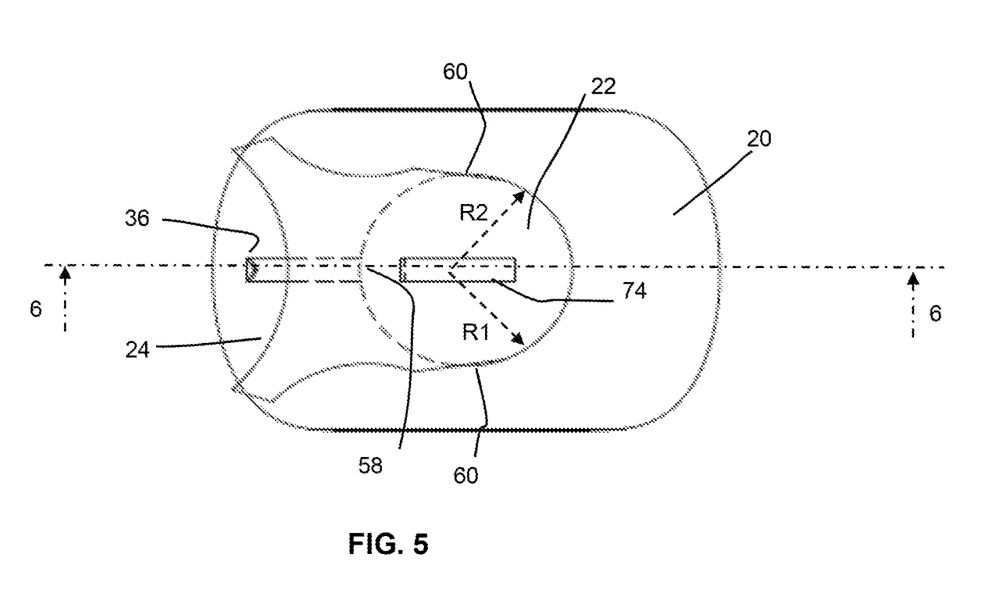
FIG. 5 is a bottom view of the anchor of the anastomosis device of FIG. 1.
Figure 6:
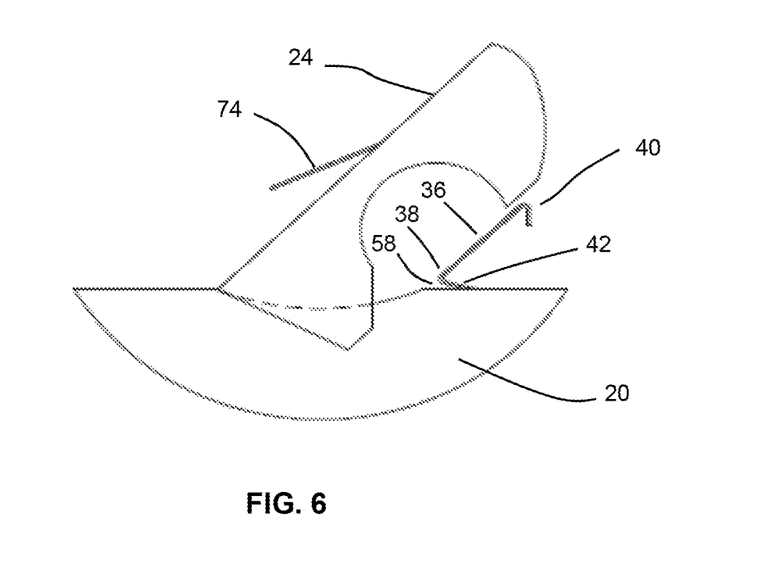
FIG. 6 is a cross-sectional view of the anchor of the anastomosis device of FIG. 5 taken along the 6-6 axis.

As depicted in, for example FIGS. 3 and 5, the opening 22 in the curved base 20 may be a substantially circular opening defined by a radius R1. The curved sides 32, 34 of the riser 24 may have a radius R2 of curvature. The radius R2 of curvature of the curved sides 32, 34 of the riser 24 may be similar, including substantially equal, to the radius R1 of the opening 22 of the base 20. If desired, this curvature may be changed over its length, thus varying the radii or radiuses as well.

The riser 24 and the hook member 36 may be welded to the curved base 20 of the anchor 14. As depicted in FIG. 5, the hook member 36 includes a hook base 42 which is securably disposed, for example by welding, to the base 20 and the first orifice wall portion 58. The side walls 32, 34 of the riser portion 24 at the first end 62 of the riser 24 may be securably disposed, for example by welding, to the base 20 of the anchor 14 at selected locations. For example, the side walls 32, 34 of the riser portion 24 at the first end 62 of the riser 24 may be secured proximal to orifice wall portions 60. While two such securement locations are depicted in FIG. 5, any suitable number of securement locations may be used, including just one securement location or a plurality of securement locations. As depicted in FIG. 5, the generally opposed or displaced orifice wall portions 60 are disposed approximately 90 degrees from first orifice wall portion 58. Such angular displacement is non-limiting and any suitable angular displacement from 30 degrees to 120 degrees may suitably be used.

While the base 20, the riser 24, and the hook member 36 have been described as individual components securably affixed as, for example, described above, the present invention is not so limited. The base 20, the riser 24, and the hook member 36 may be a one-piece, monolithic structure. Such a one-piece, monolithic structure may be formed by laser cutting a suitable material construct, such as a tube, or by additive, three dimensional printing techniques.

Figure 7:
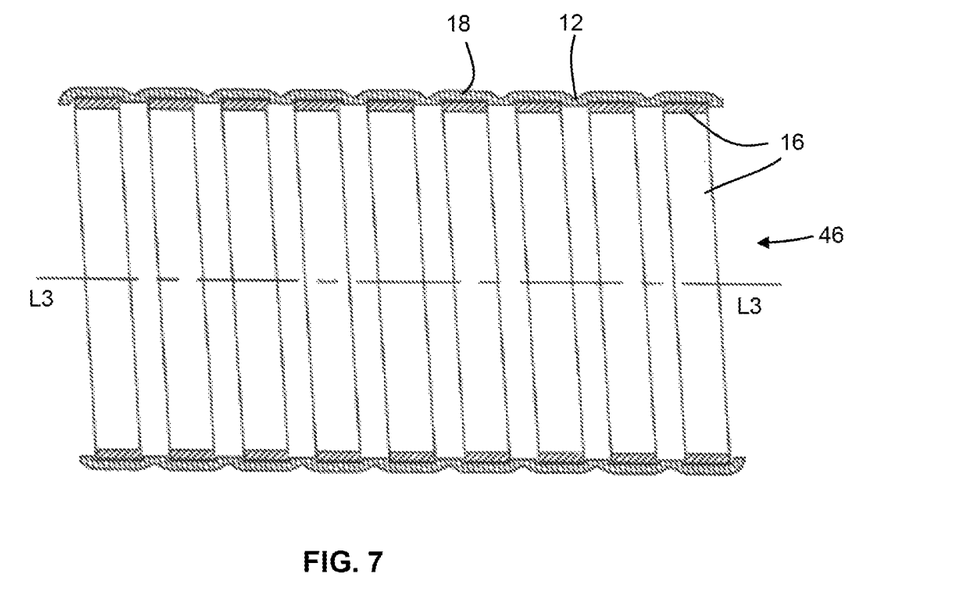
FIG. 7 depicts a stent securably disposed within the graft of FIG. 1.
Figure 8:
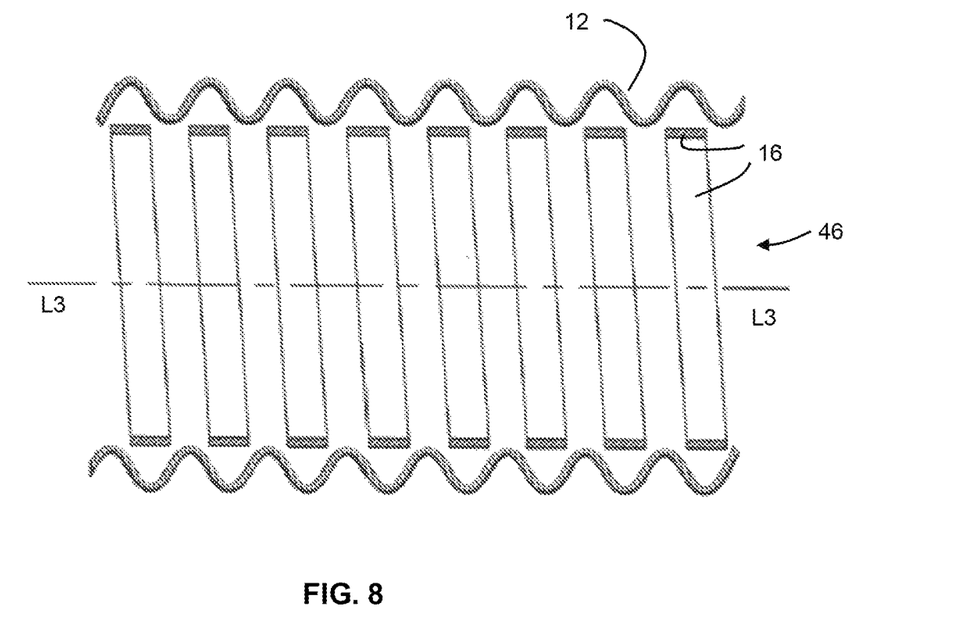
FIG. 8 depicts the stent and graft of FIG. 7 prior to securement of the stent to the graft.

The graft 12, the stent 16, and the stent-graft 18 are further depicted in FIGS. 7 and 7. FIGS. 7 and 8 are cross-sectional views. The stent-graft 18 has an open lumen 46 defining a longitudinal axis L3.

As depicted in FIG. 7, stent-graft 18 includes a stent 16 securably disposed within the graft 12. The stent 16 is depicted as being a coil or tubular stent having a spiral winding of a metallic ribbon or metallic wire. The tubular stent 16 is disposed within at least a portion of the graft 12. The graft 12 may have a textile construction of knitted or woven yarns. Desirably, the graft 12 may have a textile construction of woven yarns. One useful type of yarns includes poly(ethylene terephthalate) or PET yarns. Desirably, the PET yarns are texturized PET yarns.

The graft 12 is securably disposed over the stent 16. Desirably, the stent-graft 18 may be free of sutures and other conventional attachment techniques or devices described above between the graft 12 and the stent 16. Moreover, the stent-graft 18 may be free of adhesives between the graft 12 and the stent 16. The graft 12 may be secured to the stent 16 through chemical shrinkage techniques. For example, the coil stent 16 may be disposed on a mandrel (not shown). A crimped graft 12 (see FIG. 8) may then be disposed over the mandrel and the coil stent 16. The crimped graft 12 may then be secured to the coil stent 16 through chemical shrinkage techniques. Such chemical shrinkage techniques may include the use of methyl chloride at elevated temperatures, such as from about 200° F. (about 93° C.) to about 250° F.

(about 121° C.) for moderate periods of time, for example from 45 minutes to 60 minutes.

The anastomosis devise of the present invention is not limited to the use of just one anchor 14 for securably receiving one end of the graft 12 or end of the stent-graft 18. The graft 12 or the stent-graft 18 may have an anchor 14 disposed at each opposed end of the graft 12 or the stent-graft 18.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

The following embodiments or aspects of the invention may be combined in any fashion and combination and be within the scope of the present invention, as follows:

Embodiment 1

An anastomosis device (10) comprising:
an anchor (14) comprising a base (20) with an opening and a riser portion (24) securably associated with the base (20), the base (20) being configured to be disposed within a body lumen, the riser portion (24) having at least one attachment point (26, 28); and
a tubular and hollow graft (12) secured directly to the at least one attachment point (26, 28) of the riser portion (24), the at least one attachment point (26, 28) of the riser portion (24) being free of sutures or pins traversing portions of the graft (12) proximal the riser portion (24).

Embodiment 2

The anastomosis device (10) of embodiment 1, further comprising:
a tubular stent (16) disposed within at least a portion of the graft (12) to provide a stent-graft (18).

Embodiment 3

The anastomosis device (10) of embodiment 2, wherein the tubular stent (16) is a coil stent.

Embodiment 4

The anastomosis device (10) of any preceding embodiments, wherein the graft (12) has a textile construction of knitted or woven yarns.

Embodiment 5

The anastomosis device (10) of embodiments 2-4, wherein the graft (12) is securably disposed over the stent (16) and is free of sutures, staples, pins, and adhesives between the graft (12) and the stent (16).

Embodiment 6

The anastomosis device (10) of any preceding embodiments, wherein the at least one of attachment point (26, 28) is a detent having a tip (30) directed towards the base (20).

Embodiment 7

The anastomosis device of any preceding embodiments, further comprising at least two attachment points (26, 28), each of the at least two attachment points (26, 28) being a detent having a tip (30) disposed in a direction towards the base (20).

Embodiment 8

The anastomosis device of embodiment 7, wherein the at least two attachment points (26, 28) are disposed on opposing sides (32, 34) of the riser portion (24).

Embodiment 9

The anastomosis device (10) of any preceding embodiments, further comprising:
an elongate hook member (36), the elongate hook member (36) comprising opposed first and second ends (38, 40), the first opposed end (38) comprising a hook base (42) secured to the base (20) of the anchor (14), the second opposed end (38) having a pointed tip (44) disposed in a direction towards the base (20).

Embodiment 10

The anastomosis device (10) of any preceding embodiments, further comprising an arm (74) having a first end (76) secured to a portion (72) of an outer surface (82) of the riser portion (24) and a second end (78) disposed away from the outer surface (82) of the riser portion (24).

Embodiment 11

An anastomosis device (10) comprising:
(a) an anchor (14) comprising:
(i) an elongate and curved base (20) comprising:
first and second opposed ends (48, 50) defining a longitudinal axis (L1) therein between and curved sides (52, 54) disposed downwardly from the longitudinal axis (L1) of the base (20);
an opening (22) disposed between the first and second opposed ends (48, 50), the opening (22) being defined by an orifice wall boundary (56), the orifice wall boundary (56) having first and second generally opposed or displaced orifice wall portions (58, 60);
(ii) a hook member (36) securably disposed to the curved base (20) proximal to the first opposed orifice wall portion (58);
(iii) an elongate curved riser (24) comprising:
first and second opposed ends (62, 64) defining a longitudinal axis (L2) therein between, the first opposed end (62) of the riser (24) being disposed to the base (20) proximal to the second opposed orifice wall portions (60); and
first and second opposed curved sides (32, 34) disposed downwardly from the longitudinal axis (L2) of the riser (24), the first and second opposed sides (32, 34) each having a terminal anchoring point (26, 28); and
(b) a tubular and hollow graft (12) secured to the anchor (14) at the hook member (36) and at the terminal anchoring points (26, 28) of the riser (24).

Embodiment 12

The anastomosis device (10) of embodiment 11,
wherein the opening (22) in the curved base (20) is a substantially circular opening defined by a radius (R1); and wherein the curved sides (32, 34) of the riser (24) have a radius (R2) of curvature substantially equal to the radius (R1) of the opening (22).

Embodiment 13

The anastomosis device (10) of embodiments 11-12, wherein the graft (12) is free of sutures, staples, pins, and adhesives at graft portions (66) proximal to the anchor (14).

Embodiment 14

The anastomosis device (10) of embodiments 11-13, wherein the hook member (36) comprises a base portion (42) securably disposed to the curved base (20) of the anchor (14) and an opposed tip portion (44) with the graft (12) being secured thereat; and wherein the opposed tip portion (44) is disposed in a direction towards the base (20) of the anchor (14).

Embodiment 15

The anastomosis device (10) of embodiments 11-13, further comprising an arm (74) having a first end (76) secured to a portion (72) of an outer surface (82) of the riser (24) and a second end (78) disposed away from the outer surface (82) of the riser (24).

Embodiment 16

The anastomosis device (10) of embodiments 11-15, wherein the curved base (20), the riser (24), and the hook member (36), and optionally the arm (74), comprise a biocompatible metallic material.

Embodiment 17

The anastomosis device (10) of embodiment 16, wherein the metallic material comprises a nickel-titanium alloy.

Embodiment 18

The anastomosis device (10) of embodiment 16-17, wherein the riser (24) and the hook member (36) are welded to the curved base (20).

Embodiment 19

The anastomosis device (10) of embodiments 16-17, wherein the curved base (20), the riser (24), and the hook member (36), and optionally the arm (74), are a one-piece, monolithic structure.

Embodiment 20

The anastomosis device (10) of embodiments 11-19, further comprising:
a tubular stent (16) disposed within at least a portion of the graft (12).

Embodiment 21

The anastomosis device (10) of embodiment 20, wherein the tubular stent (16) is a coil stent.

Embodiment 22

The anastomosis device (10) of embodiments 11-21, wherein the graft (12) has a textile construction of knitted or woven yarns.

Embodiment 23

The anastomosis device (10) of embodiment 20, wherein the graft (12) is securably disposed over the stent (16) and is free of sutures, staples, pins, and adhesives between the graft (12) and the stent (16).

Embodiment 24

An anastomosis device (10) comprising:
(a) an anchor (14) comprising:
(i) an elongate and curved base (20) comprising:
first and second opposed ends (48, 50) defining a longitudinal axis (L1) therein between and curved sides (52, 54) disposed downwardly from the longitudinal axis (L1) of the base (20);
an opening (22) disposed between the first and second opposed ends (48, 50), the opening (22) being defined by an orifice wall boundary (56), the orifice wall boundary (56) having first and second generally opposed or displaced orifice wall portions (58, 60);
(ii) a hook member (36) securably disposed to the curved base (20) proximal to the first opposed orifice wall portion (58);
(iii) an elongate curved riser (24) comprising:
first and second opposed ends (62, 64) defining a longitudinal axis (L2) therein between, the first opposed end (62) of the riser (24) being disposed to the base (20) proximal to the second opposed orifice wall portions (60); and
first and second opposed curved sides (32, 34) disposed downwardly from the longitudinal axis (L2) of the riser (24), the first and second opposed sides (32, 34) each having a terminal anchoring point (26, 28);
(iv) an arm (74) having a first end (76) secured to a portion (72) of an outer surface (82) of the riser (24) and a second end (78) disposed away from the outer surface (82) of the riser (24); and
(b) a tubular and hollow graft (12) secured to the anchor (14) at the hook member (36) and at the terminal anchoring points (26, 28) of the riser (24), and at the second end (78) of the arm (74).

What is claimed is:

1. An anastomosis device comprising:
(a) an anchor comprising:
(i) an elongate and curved base comprising:
first and second opposed ends defining a longitudinal axis therein between and curved sides disposed downwardly from the longitudinal axis of the base;
an opening disposed between the first and second opposed ends, the opening being defined by an orifice wall boundary, the orifice wall boundary having first and second generally opposed or displaced orifice wall portions;
(ii) a hook member securably disposed to the curved base proximal to the first generally opposed or displaced orifice wall portion;
(iii) an elongate curved riser comprising:
first and second opposed ends defining a longitudinal axis therein between, the first opposed end of the riser being disposed to the base proximal to the second generally opposed or displaced orifice wall portion; and first and second opposed curved sides disposed downwardly from the longitudinal axis of the riser, the first and second opposed curved sides each having a terminal anchoring point; and (b) a tubular and hollow graft secured to the anchor at the hook member and at the terminal anchoring points of the riser.

2. The anastomosis device of claim 1, wherein the opening in the curved base is a substantially circular opening defined by a radius; and wherein the curved sides of the riser have a radius of curvature substantially equal to the radius of the opening.

3. The anastomosis device of claim 1, wherein the graft is free of sutures, staples, pins, and adhesives at graft portions proximal to the anchor.

4. The anastomosis device of claim 1, wherein the hook member comprises a base portion securably disposed to the curved base of the anchor and an opposed tip portion with the graft being secured thereat; and wherein the opposed tip portion is disposed in a direction towards the base of the anchor.

5. The anastomosis device of claim 1, further comprising an arm having a first end secured to a portion of an outer surface of the riser and a second end disposed away from the outer surface of the riser.

6. The anastomosis device of claim 1, wherein the curved base, the riser, and the hook member comprise a biocompatible metallic material.

7. The anastomosis device of claim 6, wherein the metallic material comprises a nickel-titanium alloy.

8. The anastomosis device of claim 6, wherein the riser and the hook member are welded to the curved base.

9. The anastomosis device of claim 6, wherein the curved base, the riser, and the hook member are one-piece, monolithic structure.

10. The anastomosis device of claim 1, further comprising:

a tubular stent disposed within portions of the graft.

11. The anastomosis device of claim 10, wherein the tubular stent is a coil stent.

12. The anastomosis device of claim 1, wherein the graft has a textile construction of knitted or woven yarns.

13. The anastomosis device of claim 12, wherein the graft is securably disposed over a stent and is free of sutures, staples, pins, and adhesives between the graft and the stent.

14. An anastomosis device comprising:

(a) an anchor comprising:

(i) an elongate and curved base comprising:

first and second opposed ends defining a longitudinal axis therein between and curved sides disposed downwardly from the longitudinal axis of the base;

an opening disposed between the first and second opposed ends, the opening being defined by an orifice wall boundary, the orifice wall boundary having first and second generally opposed or displaced orifice wall portions;

(ii) a hook member securably disposed to the curved base proximal to the first generally opposed or displaced orifice wall portion;

(iii) an elongate curved riser comprising:

first and second opposed ends defining a longitudinal axis therein between, the first opposed end of the riser being disposed to the base proximal to the second generally opposed or displaced orifice wall portion; and first and second opposed curved sides disposed downwardly from the longitudinal axis of the riser, the first and second opposed curved sides each having a terminal anchoring point;

(iv) an arm having a first end secured to a portion of an outer surface of the riser and a second end disposed away from the outer surface of the riser; and (b) a tubular and hollow graft secured to the anchor at the hook member, at the terminal anchoring points of the riser, and at the second end of the arm.

15. The anastomosis device of claim 14, further comprising:

a tubular stent disposed within at least a portion of the graft to provide a stent-graft.

16. The anastomosis device of claim 15, wherein the tubular stent is a coil stent.

17. The anastomosis device of claim 15, wherein the graft is securably disposed over the stent and is free of sutures, staples, pins, and adhesives between the graft and the stent.

18. The anastomosis device of claim 14, wherein the graft has a textile construction of knitted or woven yarns.

\* \* \* \* \*